US009810682B1

(12) United States Patent
Barry

(10) Patent No.: US 9,810,682 B1
(45) Date of Patent: Nov. 7, 2017

(54) BREATH TEST SIMULATOR WITH HEADSPACE FAN AND METHOD

(71) Applicant: Guth Laboratories, Inc., Harrisburg, PA (US)

(72) Inventor: Shawn P. Barry, Millersburg, PA (US)

(73) Assignee: Guth Laboratories, Inc., Harrisburg, PA (US)

( * ) Notice: Subject to any disclaimer, the term of this patent is extended or adjusted under 35 U.S.C. 154(b) by 400 days.

(21) Appl. No.: 14/618,626

(22) Filed: Feb. 10, 2015

Related U.S. Application Data

(60) Provisional application No. 61/973,900, filed on Apr. 2, 2014.

(51) Int. Cl.
*G01N 33/00* (2006.01)
*G01N 33/497* (2006.01)

(52) U.S. Cl.
CPC ................ *G01N 33/4972* (2013.01)

(58) Field of Classification Search
CPC .................................................. G01N 33/0006
See application file for complete search history.

(56) References Cited

U.S. PATENT DOCUMENTS 6,526,802 B1 * 3/2003 Fisher ................ G01N 33/4972
366/273
7,493,793 B2 2/2009 Guth et al.
7,895,878 B1 3/2011 Guth et al.

OTHER PUBLICATIONS

Alcohol Countermeasure Systems Corp., print cut of website page (http://acs-corp.com/products/accessories/calibration-equipment/), "Calibration Equipment—Breath Alcohol Simulator," printed prior to Apr. 2014.

* cited by examiner

Primary Examiner — Robert R Raevis
(74) Attorney, Agent, or Firm — Hooker & Habib, P.C.

(57) ABSTRACT

A breath test simulator includes a jar holding an ethyl alcohol/water solution. A heated metal top housing on the top of the jar supports a baffle plate extending over the solution. Ethyl alcohol/water vapor is flowed from the solution into a headspace between the baffle plate and the top housing. A rotary fan in the headspace circulates vapor in the headspace and moves the vapor against the housing to heat the vapor. The heated vapor is circulated and heats the jar to speed warm up of the simulator and assure the headspace vapor is maintained at a desired temperature prior to discharge to a breath test instrument to be calibrated.

19 Claims, 3 Drawing Sheets

BREATH TEST SIMULATOR WITH HEADSPACE FAN AND METHOD

The disclosure relates to a breath test simulator and method that rapidly generates an ethyl alcohol/water vapor sample having a desired alcohol concentration which is heated to a desired temperature. The simulator creates the vapor sample in a headspace and flows the vapor sample to a breath test analyzer for calibrating the analyzer. A fan in the simulator headspace circulates vapor in the headspace against a heated wall to heat the vapor and then circulates the heated vapor against an unheated wall of the headspace to rapidly heat the unheated wall to an operating temperature and assure that the vapor sample is heated to a desired temperature and has a proper alcohol concentration.

Circulation of the vapor in the headspace by the fan rapidly warms an unheated wall of the headspace to a desired operating temperature. The cold-start warm-up time for the simulator is reduced.

DETAILED DESCRIPTION OF THE DISCLOSURE

Figure 1:
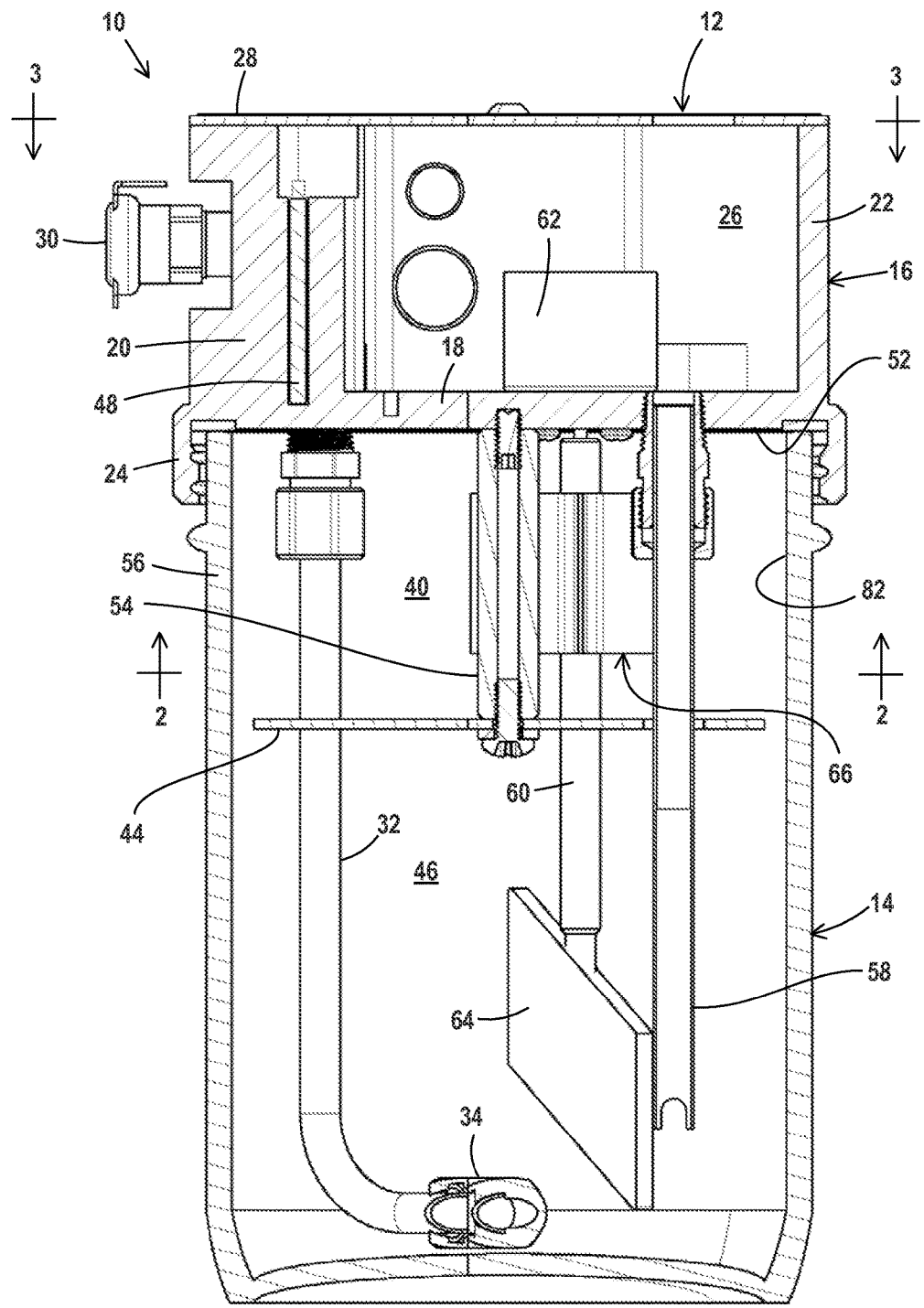
FIG. 1 is a vertical section through a breath test simulator taken along line 1-1 of FIG. 2.

Breath test simulator 10 includes a top housing 12 and a cylindrical plastic or glass jar 14 threadably mounted on the bottom of the top housing. The housing 12 includes a metal body 16 forming a lid 18 overlying the top of the jar, an elevated projection 20 extending above the lid on one side of the top housing, a semi-circular wall 22 extending around the housing between the ends of projection 20 and an inwardly threaded attachment collar 24 extending around and down from lid 18 to engage complementary threads on the outer surface of the top of the jar. Body 16 defines an interior space 26 above lid 18 surrounded by wall 22 and projection 20. A thin, removable metal lid 28 is mounted on the top of body 16 and overlies space 26.

Figure 2:
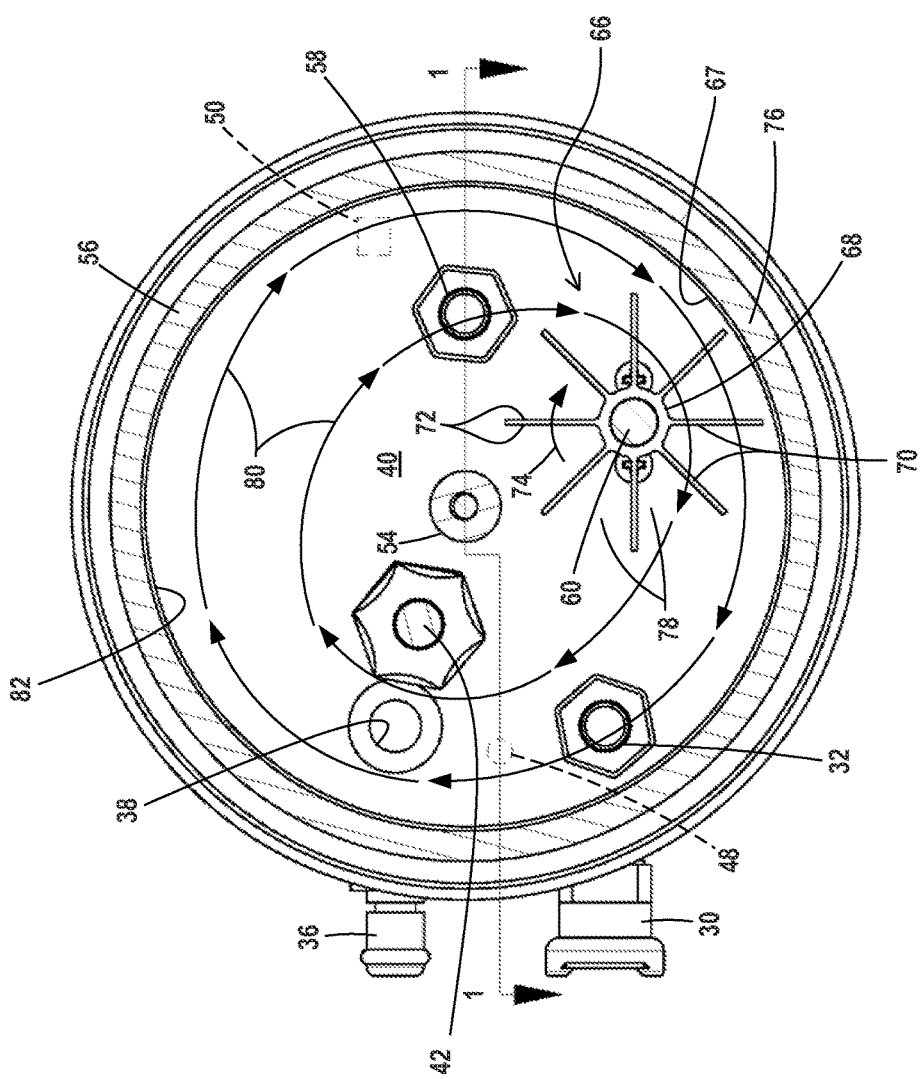
FIG. 2 is a horizontal sectional view taken along line 2-2 of FIG. 1.
Figure 3:
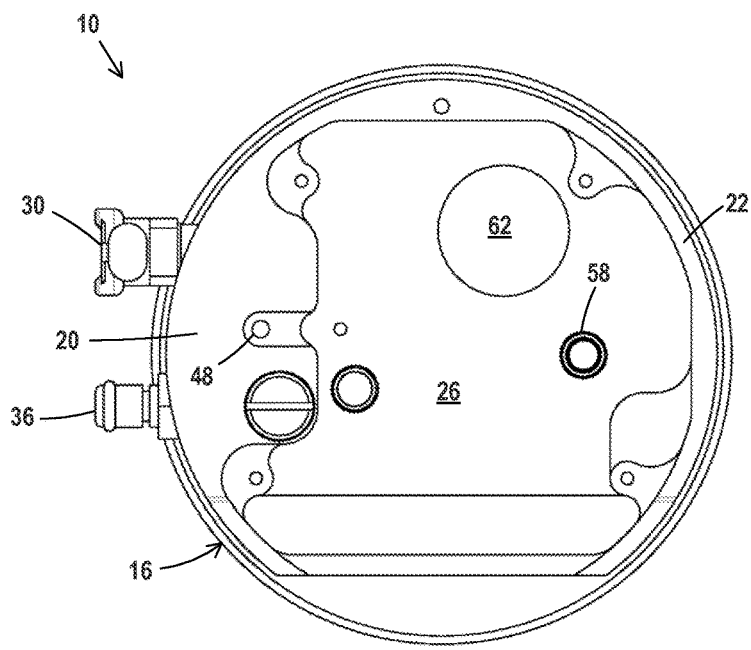
FIG. 3 is a view taken along line 3-3 of FIG. 1.

Top housing 12 supports a number of components which extend from lid 18 into the interior of jar 14, as shown in FIGS. 1 and 2. Air inlet port 30, mounted on projection 20 above lid 18, is connected to air inlet tube 32 which extends down from the lid and into the interior of the jar to bubbler outlet 34 at the bottom of the jar. A passage in projection 20 connects the inlet port 30 to tube 32. Vapor outlet port 36 is mounted on projection 20 adjacent inlet port 30 and is connected to a passage in projection 20 extending to vapor discharge opening 38 in lid 18 at the top of jar 14. Vapor from headspace 40 flows through opening 38 to port 36.

Heater rod 42 is mounted on lid 18 and extends down into jar 14 past baffle plate 44. An electric heating element at the lower end of rod 42 heats ethyl alcohol/water solution 46 in the bottom of the jar.

Electric resistance heater 48 is mounted in projection 20 to heat projection 20 and lid 18 by conduction through metal body 16. A temperature sensor 50 is mounted in lid 18 across the lid from projection 20 and heater 48. See FIG. 2. The lower surface 52 of lid 18 is heated by heater 48. The temperature of the lower surface is greater adjacent the heater than away from the heater. Control circuits for actuating the heater in rod 42 and heater 48 are mounted in space 26 to maintain the temperature of the solution 46 within a desired temperature range and to maintain the temperature of the vapor in headspace 40 within a desired temperature range.

Circular baffle plate 44 extends across the interior of jar 14 a short distance above the top surface of ethyl alcohol/water solution 46 in the bottom of the jar. Plate 44 is mounted on support post 54 secured to the undersurface of lid 18. Headspace 40 is located between plate 44 and lid 18 and top portion 56 of cylindrical jar 14.

Temperature sensor rod 58, shown in FIG. 2, is mounted on lid 18 and extends into the solution 46 in the bottom of jar 14. Redundant temperature sensors are mounted on the lower end of rod 58 for sensing the temperature of solution 46.

Stirrer rod 60 is attached to the output shaft of electric stirrer motor 62 mounted on the top surface of lid 18 in space 26, as shown in FIG. 1. Rod 60 extends down from lid 18, through headspace 40, through a stirrer rod opening in baffle plate 44 and into the alcohol/water solution 46 in the bottom of jar 14. A flat stirrer or agitator 64 is mounted on the lower end of rod 60 in solution 46. Motor 62 rotates rod 60 and stirrer 64 to stir the solution 46 during the operation of simulator 10.

A rotary paddle wheel-type fan 66 is mounted on rod 60 in the center of headspace 40. The fan is located approximately equidistant between lid 18 and plate 44. Fan 66 includes a hub surrounding cylindrical rod 60 and eight circumferentially spaced vanes 70 extending outwardly from the center of the hub. As shown in FIG. 2, the vanes have parallel sidewalls 72 and a uniform, narrow thickness of about 0.032 inches. Vanes 70 are spaced apart at 45° around rod 60.

The height of headspace 40 between plate 44 and lid 18 is about 1.8 inches. Headspace 40 has an interior diameter of about 3.5 inches. The diameter of fan 66, measured between the ends of opposed vanes 70, is about 1.375 inches. Fan 66 has a vertical height 68 of about 1.0 inches. During operation of simulator 10, motor 62 rotates rod 60 and fan 66 in the direction of arrow 74, shown in FIG. 2, at a speed of about 800 rpm. Rod 60 is adjacent one side of the headspace with the ends of vanes 70 spaced from the jar a short distance 67 of 0.125 inches.

Fan 66, rod 60 and stirrer 64 are preferably manufactured from a single body of fused thermoplastic material using three-dimension computer printing technology. If desired, the fan, rod and stirrer may be manufactured separately from other types of materials and assembled after manufacture.

The thin, uniform-thickness vanes 70 increase the size of the V-shaped recesses 78 between adjacent vanes 70 to increase the volumetric efficiency of the rotating fan in circulating alcohol/water vapor throughout headspace 40. Vanes 70 are preferably flat. However, curved vanes may be used, if desired.

FIG. 2 illustrates that rotation of fan 66 in the direction of arrow 74 flows the alcohol/water vapor in the headspace 40 around the headspace as indicated by representational flow lines 80. The vapor flows around the headspace in the same direction as the rotation of the fan. The rotating vapor contacts lid 18 and plate 44 and is thrown radially outwardly against top portion 56 of the jar.

Rotation of fan 66 captures vapor between hub 68 and the adjacent wall of the jar and circulates the vapor around the headspace. The vapor flows around the headspace in the same direction as the direction of rotation of fan 66 indicated by arrow 74.

Positioning of fan 66 adjacent to the interior surface 82 of the jar assures that the fan captures the vapor between the hub and the jar and flows the vapor around the headspace. The rotation of fan 66 flows the vapor upwardly from the fan and against lid bottom surface 52. Contact with bottom surface 52 heats the vapor. The heated vapor is rapidly flowed radially outwardly against jar surface 82 and heats the top portion 56 of the jar.

Operation of simulator 10 will now be described.

Jar 14 is filled with an appropriate volume of ethyl alcohol/water solution up to a level slightly below plate 44. The simulator vapor outlet port 36 is connected to the vapor inlet port of the breath test analyzer to be calibrated. The air inlet port 30 is connected to a tube for delivery of breath sample air to the simulator to generate a volume of heated vapor saturated with a known concentration of ethyl alcohol.

The stirrer motor 62 is actuated to rotate stirrer rod 60, stirrer 64 and fan 66. The circuits for the heaters on rod 42 and heater 48 are actuated to heat the solution 46 in the bottom of the jar and to heat projection 20 and lid 18 to stable operating temperatures. The operation of the heaters and the control circuits are described more fully in U.S. Pat. No. 7,895,878, assigned to Guth Laboratories, Inc. of Harrisburg, Pa., USA.

In simulator 10, the temperature of solution 46 is heated to a solution temperature of 34° C.+/− a small temperature tolerance. Heater 48 heats the lid 18 until sensor 50 is at a temperature of about 35° C. After warm up, heat radiating from the heater 48 heats the lid bottom surface 52 facing headspace 26 and heats the ethyl alcohol/water vapor in the headspace to a uniform temperature of 34° C.

During warm up of simulator 10, the glass at the jar top portion 56 forming the outer wall of headspace 26 is at ambient temperature which is lower than 34° C. The low temperature of the jar may cause the alcohol/water solution in the headspace to condense on the inner jar surface 82.

Fan 66 circulates the alcohol/water vapor around the headspace, as previously described. The vapor is flowed up against the lower surface 52 of lid 18 and is heated by the lid. The fan flows the heated vapor from the lid against the interior surface 82 of top portion 56 of the jar to rapidly warm portion 56 to an operating temperature essentially equal to the desired temperature of the vapor in the headspace.

Circulation of the vapor in the headspace by the fan against the lid lower surface 52 heats the vapor and eliminates a temperature gradient in the headspace between the top and bottom of the headspace. Baffle plate 44, which may be made of a thermoplastic material, is also heated by circulation of the heated vapor in the headspace by fan 66.

Figure 5:
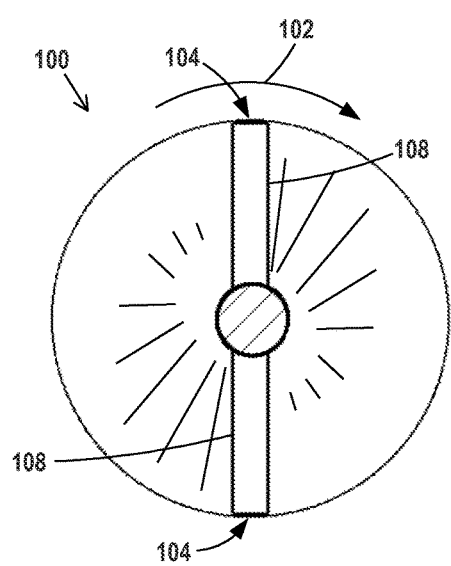
FIG. 5 is a view taken along line 5-5 in FIG. 4.
Figure 4:
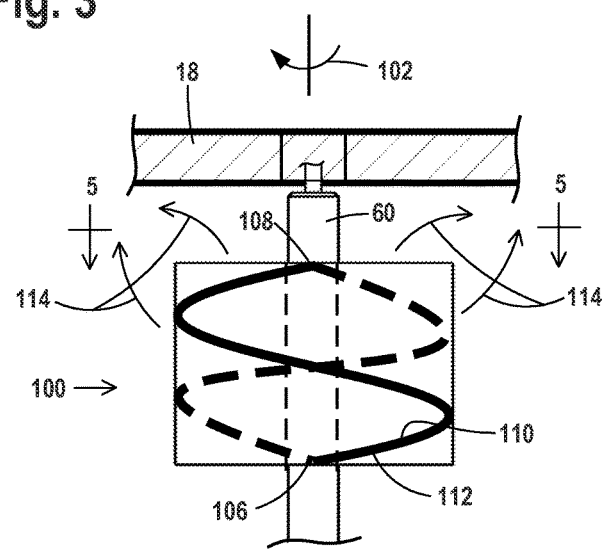
FIG. 4 is a view of an alternative fan in the headspace.

FIGS. 4 and 5 relate to a breath test simulator similar to simulator 10 but with a different fan 100 mounted on stirrer rod 60. Stirrer motor 62 rotates rod 60 and fan 100 in the direction of arrow 102, shown in FIGS. 4 and 5. Fan 100 and rod 60 may be manufactured from integral body, as previously described, or may be manufactured from separate parts which are assembled.

Fan 100 includes two spiral vanes 104 extending around rod 60 similar to the spiral vanes of a corkscrew. Each vane 104 has a lower leading edge 106 at the bottom of the fan and an upper trailing edge 108 at the top of the fan. Upper and lower spiral surfaces 110 and 112 extend between the lower and upper edges of the vanes. Each vane extends 360° around the axis of the fan between edges 106 and 108. Upper lift surfaces 110 flow vapor up against the heated lid 18.

Rotation of fan 100 by motor 62 captures vapor between the fan and interior surface 82 and forces the vapor up and outwardly from the fan along upwardly extending representational flow lines 114 so that the vapor is flowed directly against the heated lower surface 52 of lid 18 and is heated by the lid. The rotation of the fan flows the heated vapor outwardly against the jar surface 82 to heat the upper portion of the jar 56 to desired operational temperature for the simulator.

What is claimed is:

1. A breath test simulator for supplying breath test vapor to a breath test instrument to be calibrated, the simulator comprising; a jar; a housing on the top of the jar, the housing including a metal lid overlying the top of the jar; an ethyl alcohol/water solution in the bottom of the jar; a baffle plate above the alcohol/water solution; a headspace between the baffle plate and the lid; ethyl alcohol/water vapor in the headspace; a heater in the top housing to flow heat to the lid; an air inlet port in the top housing; an air inlet tube extending from the air inlet port into the alcohol/water solution in the jar to flow air into the solution; an outlet port on the top housing and a passage extending from an opening in the lid at the headspace to the outlet port; a solution stirrer in the alcohol/water solution in the bottom of the jar; a motor on the top housing, a vapor fan in the headspace, and a rotary operative connection between the motor and the fan; wherein the heater heats the metal lid at the top of the headspace and the motor rotates the fan in the headspace to circulate the vapor in the headspace against the lid, the lid heats the vapor and the vapor heats the top of the jar at the headspace to an operating temperature.

2. The simulator as in claim 1 wherein the fan includes a vapor lift surface.

3. The simulator as in claim 1 wherein the fan includes a plurality of vanes.

4. The simulator as in claim 2 wherein said vanes are spaced around the circumference of the fan and are separated by recesses.

5. The simulator as in claim 4 wherein the recesses are V-shaped.

6. The simulator as in claim 5 wherein the vanes have a thin, uniform thickness and flat opposed sidewalls.

7. The simulator as in claim 1 wherein the rotary operative connection including a stirrer rod extending through the headspace and into the alcohol/water solution in the bottom of the jar, the upper end of the stirrer rod connected to the motor, said fan on said stirrer rod, and the motor rotating the rod and fan at about 800 rpm.

8. The simulator as in claim 7 wherein said fan includes a plurality of circumferentially spaced vanes, said stirrer rod located adjacent the interior surface of the jar, rotation of said stirrer rod moving the outer ends of the vanes closely adjacent to the interior surface of the jar to capture vapor between the vanes.

9. The simulator as in claim 1 including a circumferential flow of vapor around the headspace in the direction of rotation of the fan.

10. The simulator as in claim 1 wherein said fan and stirrer rod are integrally formed from thermoplastic material.

11. The simulator as in claim 1 wherein said fan includes eight vanes each spaced apart 45° around the fan, said vanes defining eight V-shaped recesses between adjacent vanes.

12. The simulator as in claim 11 wherein said vanes have a narrow, uniform thickness and said fan is located adjacent an interior wall of the jar so that rotation of the fan sweeps the ends of the vanes close to the wall to capture vapor between the vanes.

13. A breath test simulator for supplying breath test vapor to a breath test instrument to be calibrated, the simulator comprising: a headspace having a metal heated interior wall and an unheated interior wall, ethyl alcohol/water vapor in the headspace; a source of ethyl alcohol/water vapor connected to the headspace, the source including an ethyl alcohol/water solution and air flowed through the solution to generate the ethyl alcohol/water vapor; a heater to heat the wall; and a vapor fan in the headspace operable to circulate vapor in the headspace against the heated wall so that the heated wall heats the vapor and to circulate the heated vapor against the unheated wall to heat the unheated wall.

14. A simulator as in claim 13 wherein said vapor fan is a rotary fan and including a motor on the simulator having an output rod extending into the headspace, said fan mounted on said rod.

15. The simulator as in claim 14 wherein the fan includes a plurality of vanes.

16. The simulator as in claim 14 wherein the fan includes a vapor lift surface and the metal wall is located above the fan so that the fan flows vapor up and into contact with the metal wall.

17. A method of generating a breath test vapor for calibrating a breath test instrument, comprising the steps of,
   A. providing a simulator having a headspace with a heated metal lid at the top of the headspace, a circumferential portion of a jar secured to the lid, and an ethyl alcohol/water solution in the jar,
   B. flowing alcohol/water vapor from the solution into the headspace,
   C. rotating a fan in the headspace to move the alcohol/water vapor in the headspace and against the heated lid, transferring heat from the lid to the vapor to heat the vapor, and moving the heated vapor against the jar to heat the jar, and
   D. flowing heated alcohol/water vapor from the headspace to the breath instrument to be calibrated.

18. The method of claim 17 including the steps of:
   E. providing a circumferential fan having a plurality of outwardly extending vanes spaced around the fan in the headspace adjacent the interior wall of the jar, and
   F. rotating the fan to move the ends of vanes adjacent the sidewall of the jar to circulate the vapor around the headspace.

19. The method of claim 17 including the step of:
   E. rotating the fan to move vapor in the headspace up and into contact with the lid.

* * * * *